United States Patent
Kotha et al.

(10) Patent No.: US 7,448,389 B1
(45) Date of Patent: Nov. 11, 2008

(54) METHOD AND KIT FOR INDUCING HYPOXIA IN TUMORS THROUGH THE USE OF A MAGNETIC FLUID

(75) Inventors: Sanjay Kotha, Falls Church, VA (US); Tirumalai S. Sudarshan, Vienna, VA (US)

(73) Assignee: Materials Modification, Inc., Fairfax, VA (US)

( * ) Notice: Subject to any disclaimer, the term of this patent is extended or adjusted under 35 U.S.C. 154(b) by 576 days.

(21) Appl. No.: 10/681,899

(22) Filed: Oct. 10, 2003

(51) Int. Cl.
*A61B 19/00* (2006.01)

(52) U.S. Cl. ............................................. 128/898

(58) Field of Classification Search ............ 600/1–15; 128/897–899
See application file for complete search history.

(56) References Cited

U.S. PATENT DOCUMENTS

| | | | |
|---|---|---|---|
| 3,047,507 A | 7/1962 | Winslow | |
| 3,127,528 A | 3/1964 | Lary et al. | |
| 3,287,677 A | 11/1966 | Mohr | |
| 3,488,531 A | 1/1970 | Rosensweig | |
| 3,560,378 A | 2/1971 | Weiss et al. | |
| 3,767,783 A | 10/1973 | Sweeny et al. | |
| 3,927,329 A | 12/1975 | Fawcett et al. | |
| 3,937,839 A | 2/1976 | Strike et al. | |
| 4,064,409 A | 12/1977 | Redman | |
| 4,106,488 A | 8/1978 | Gordon | |
| 4,107,288 A | 8/1978 | Oppenheim et al. | |
| 4,183,156 A | 1/1980 | Rudy | |
| 4,219,945 A | 9/1980 | Rudy | |
| 4,267,234 A | 5/1981 | Rembaum | |
| 4,268,413 A | 5/1981 | Dabisch | |
| 4,303,636 A | 12/1981 | Gordon | |
| 4,321,020 A | 3/1982 | Mittal | |
| 4,323,056 A | 4/1982 | Borrelli et al. | |
| 4,340,626 A | 7/1982 | Rudy | |
| 4,342,157 A | 8/1982 | Gilbert | |
| 4,364,377 A | * 12/1982 | Smith ........................... | 600/12 |
| 4,443,430 A | 4/1984 | Mattei et al. | |
| 4,452,773 A | 6/1984 | Molday | |
| 4,454,234 A | 6/1984 | Czerlinski | |
| 4,472,890 A | 9/1984 | Gilbert | |
| 4,501,726 A | 2/1985 | Schröder et al. | |
| 4,545,368 A | 10/1985 | Rand et al. | |
| 4,554,088 A | 11/1985 | Whitehead et al. | |
| 4,574,782 A | 3/1986 | Borrelli et al. | |
| 4,613,304 A | 9/1986 | Meyer | |

(Continued)

FOREIGN PATENT DOCUMENTS

CA    2328826  A1    3/2001

(Continued)

OTHER PUBLICATIONS

Nanostructures of gold coated Iron core-shell nanoparticles and the nanobands assembled under magnetic field. Zhou et al, 2001, Eur. Phys. J. D 16. Abstract only.*

(Continued)

*Primary Examiner*—Samuel G Gilbert
(74) *Attorney, Agent, or Firm*—Dinesh Agarwal, P.C.

(57) ABSTRACT

A method and kit for inducing hypoxia in tumors includes impeding oxygen supply to non-hypoxic cells in a subject in need thereof by using a magnetic fluid.

47 Claims, 2 Drawing Sheets

U.S. PATENT DOCUMENTS

| | | |
|---|---|---|
| 4,628,037 A | 12/1986 | Chagnon et al. |
| 4,637,394 A | 1/1987 | Racz et al. |
| 4,662,359 A | 5/1987 | Gordon |
| 4,672,040 A | 6/1987 | Josephson |
| 4,695,392 A | 9/1987 | Whitehead et al. |
| 4,695,393 A | 9/1987 | Whitehead et al. |
| 4,721,618 A | 1/1988 | Giles et al. |
| 4,770,183 A | 9/1988 | Groman et al. |
| 4,834,898 A | 5/1989 | Hwang |
| 4,951,675 A | 8/1990 | Groman et al. |
| 4,992,190 A | 2/1991 | Shtarkman |
| 4,999,188 A | 3/1991 | Solodovnik et al. |
| 5,067,952 A | 11/1991 | Gudov et al. |
| 5,069,216 A | 12/1991 | Groman et al. |
| 5,079,786 A | 1/1992 | Rojas |
| 5,108,359 A | 4/1992 | Granov et al. |
| 5,161,776 A | 11/1992 | Nicholson |
| 5,178,947 A | 1/1993 | Charmot et al. |
| 5,180,583 A | 1/1993 | Hedner |
| 5,202,352 A | 4/1993 | Okada et al. |
| 5,207,675 A | 5/1993 | Canady |
| 5,236,410 A | 8/1993 | Granov et al. |
| 5,348,050 A | 9/1994 | Ashton |
| 5,354,488 A | 10/1994 | Shtarkman et al. |
| 5,358,659 A | 10/1994 | Ziolo |
| 5,374,246 A | 12/1994 | Ray |
| 5,427,767 A | 6/1995 | Kresse et al. |
| 5,466,609 A | 11/1995 | Siiman et al. |
| 5,493,792 A | 2/1996 | Bates et al. |
| 5,507,744 A | 4/1996 | Tay et al. |
| 5,525,249 A | 6/1996 | Kordonsky et al. |
| 5,549,837 A | 8/1996 | Ginder et al. |
| 5,565,215 A | 10/1996 | Gref et al. |
| 5,582,425 A | 12/1996 | Skanberg et al. |
| 5,595,735 A | 1/1997 | Saferstein et al. |
| 5,597,531 A | 1/1997 | Liberti et al. |
| 5,599,474 A | 2/1997 | Weiss et al. |
| 5,624,685 A | 4/1997 | Takahashi et al. |
| 5,635,162 A | 6/1997 | Fischer |
| 5,635,215 A | 6/1997 | Boschetti et al. |
| 5,645,849 A | 7/1997 | Pruss et al. |
| 5,646,185 A | 7/1997 | Giaccia et al. |
| 5,650,681 A | 7/1997 | DeLerno |
| 5,667,715 A | 9/1997 | Foister |
| 5,670,078 A | 9/1997 | Ziolo |
| 5,673,721 A | 10/1997 | Alcocer |
| 5,695,480 A | 12/1997 | Evans et al. |
| 5,702,630 A | 12/1997 | Sasaki et al. |
| 5,707,078 A | 1/1998 | Swanberg et al. |
| 5,707,877 A | 1/1998 | Siiman et al. |
| 5,714,829 A | 2/1998 | Guruprasad |
| 5,782,954 A | 7/1998 | Luk |
| 5,800,372 A | 9/1998 | Bell et al. |
| 5,813,142 A | 9/1998 | Demon |
| 5,900,184 A | 5/1999 | Weiss et al. |
| 5,919,490 A | 7/1999 | Zastrow et al. |
| 5,927,753 A | 7/1999 | Faigle et al. |
| 5,947,514 A | 9/1999 | Keller et al. |
| 5,958,794 A | 9/1999 | Bruxvoort et al. |
| 5,993,358 A | 11/1999 | Gureghian et al. |
| 6,013,531 A | 1/2000 | Wang et al. |
| 6,027,664 A | 2/2000 | Weiss et al. |
| 6,036,226 A | 3/2000 | Brown et al. |
| 6,036,955 A | 3/2000 | Thorpe et al. |
| 6,039,347 A | 3/2000 | Maynard |
| 6,044,866 A | 4/2000 | Rohrbeck |
| 6,051,607 A | 4/2000 | Greff |
| 6,076,852 A | 6/2000 | Faigle |
| 6,083,680 A | 7/2000 | Ito et al. |
| 6,096,021 A | 8/2000 | Helm et al. |
| 6,136,428 A | 10/2000 | Truong et al. |
| 6,149,576 A | 11/2000 | Gray et al. |
| 6,149,832 A | 11/2000 | Foister |
| 6,167,313 A | 12/2000 | Gray et al. |
| 6,186,176 B1 | 2/2001 | Gelbmann |
| 6,189,538 B1 | 2/2001 | Thorpe |
| 6,207,178 B1 | 3/2001 | Westesen et al. |
| 6,225,705 B1 | 5/2001 | Nakamats |
| 6,266,897 B1 | 7/2001 | Seydel et al. |
| 6,274,121 B1 | 8/2001 | Pilgrimm |
| 6,299,619 B1 | 10/2001 | Greene, Jr. et al. |
| 6,312,484 B1 | 11/2001 | Chou et al. |
| 6,315,709 B1 | 11/2001 | Garibaldi et al. |
| 6,319,599 B1 | 11/2001 | Buckley |
| 6,335,384 B1 | 1/2002 | Evans et al. |
| 6,355,275 B1 | 3/2002 | Klein |
| 6,358,196 B1 | 3/2002 | Rayman |
| 6,364,823 B1 * | 4/2002 | Garibaldi et al. ............... 600/12 |
| 6,391,343 B1 | 5/2002 | Yen |
| 6,399,317 B1 | 6/2002 | Weimer |
| 6,409,851 B1 | 6/2002 | Sethuram et al. |
| 6,443,993 B1 | 9/2002 | Koniuk |
| 6,468,730 B2 | 10/2002 | Fujiwara et al. |
| 6,475,710 B2 | 11/2002 | Kudo et al. |
| 6,481,357 B1 | 11/2002 | Lindner et al. |
| 6,489,694 B1 | 12/2002 | Chass |
| 6,527,972 B1 | 3/2003 | Fuchs et al. |
| 6,530,944 B2 | 3/2003 | West et al. |
| 6,548,264 B1 | 4/2003 | Tan et al. |
| 6,557,272 B2 | 5/2003 | Pavone |
| 6,582,429 B2 * | 6/2003 | Krishnan et al. ............... 606/41 |
| 6,663,673 B2 | 12/2003 | Christensen |
| 6,666,991 B1 | 12/2003 | Atarashi et al. |
| 6,683,333 B2 | 1/2004 | Kazlas et al. |
| 6,734,574 B2 | 5/2004 | Shin |
| 6,768,230 B2 | 7/2004 | Cheung et al. |
| 6,789,820 B2 | 9/2004 | Meduvsky et al. |
| 6,815,063 B1 | 11/2004 | Mayes |
| 6,871,871 B2 | 3/2005 | Parizat et al. |
| 6,982,501 B1 | 1/2006 | Kotha et al. |
| 7,007,972 B1 | 3/2006 | Radhakrishnan et al. |
| 7,101,862 B2 | 9/2006 | Cochrum et al. |
| 7,200,956 B1 | 4/2007 | Kotha et al. |
| 7,249,604 B1 * | 7/2007 | Mohanraj .................. 128/899 |
| 2001/0011810 A1 | 8/2001 | Saiguchi et al. |
| 2001/0016210 A1 | 8/2001 | Mathiowitz et al. |
| 2001/0033384 A1 | 10/2001 | Luo et al. |
| 2002/0045045 A1 | 4/2002 | Adams et al. |
| 2002/0164474 A1 | 11/2002 | Buckley |
| 2003/0009910 A1 | 1/2003 | Pavone |
| 2003/0216815 A1 | 11/2003 | Christensen |
| 2004/0002665 A1 | 1/2004 | Parihar et al. |
| 2004/0022849 A1 | 2/2004 | Castan et al. |
| 2004/0051283 A1 | 3/2004 | Parizat et al. |
| 2004/0132562 A1 | 7/2004 | Schwenger et al. |
| 2004/0154190 A1 | 8/2004 | Munster |

FOREIGN PATENT DOCUMENTS

| | | |
|---|---|---|
| DE | 37 38 989 A1 | 5/1999 |
| DE | 10240530 | 3/2004 |
| WO | WO 99/53901 | 10/1999 |

OTHER PUBLICATIONS

U.S. Appl. No. 10/157,921,—filed May 31, 2002.
PCT Serial No. PCT/US03/14545—Filed: May 28, 2003.
U.S. Appl. No. 10/302,962,—filed Nov. 25, 2002.
PCT Serial No. PCT/US03/16230—Filed: Jun. 25, 2003.
Sako, M et al., "Embolotherapy of hepatomas using ferromagnetic microspheres, its clinical evaluation and the prospect of its use as a vehicle in chemoembolo-hyperthermic therapy", Gan to kagaku ryoho. Cancer & chemotherapy, vol. 13, No. 4, Pt. 2, 1618-1624 (Abstract) (1986).

Australian Patent Office Examiner's Report dated May 17, 2007 (2 pages).
Derwent Abstract Accession No. 92-223333/27, JP 04149025 A (Toshiba Glass KK) May 22, 1992.
Azuma, Y. et al. "Coating of ferric oxide particles with silica by hydrolysis of TEOS", Journal of the Ceramic Society of Japan, 100(5), 646-51 (Abstract) (May 1992).
Atarashi, T. et al. "Synthesis of ethylene-glycol-based magnetic fluid using silica-coated iron particle", Journal of Magnetism and Magnetic Materials, 201, 7-10 (1999).
Homola, A. M. et al., "Novel Magnetic Dispersions Using Silica Stabilized Particles", IEEE Transactions on Magnetics, 22 (5), 716-719 (Sep. 1986).
Giri, A. et al. "AC Magnetic Properties of Compacted FeCo Nanocomposites", Mater. Phys. and Mechanics, 1, 1-10 (2000).
Sako, M. et al., "Embolotherapy of hepatomas using ferromagnetic microspheres, its clinical evaluation and the prospect of its use as a vehicle in chemoembolo-hyperthermic therapy", Gan to kagaku ryoho. Cancer & chemotherapy, vol. 13, No. 4, Pt. 2, 1618-1624 (Abstract) (1986).
Zahn, M. "Magnetic Fluid and Nanoparticle Applications to Nanotechnology", Journal of Nanoparticle Research 3, pp. 73-78, 2001.
Remington: The Science and Practice of Pharmacy, vol. II, pp. 1524-1528 (1995).
Office Action dated Jan. 20, 2004, issued in co-pending U.S. Appl. No. 10/302,962, filed Nov. 25, 2002.
Office Action dated Oct. 6, 2004, issued in co-pending U.S. Appl. No. 10/302,962, filed Nov. 25, 2002.
Office Action dated Aug. 17, 2005, issued in co-pending U.S. Appl. No. 10/302,962, filed Nov. 25, 2002.
Office Action dated May 30, 2006, issued in co-pending U.S. Appl. No. 10/302,962, filed Nov. 25, 2002.
Office Action dated Aug. 23, 2007, issued in co-pending U.S. Appl. No. 10/302,962, filed Nov. 25, 2002.
Office Action dated Jun. 13, 2008, issued in co-pending U.S. Appl. No. 10/302,962, filed Nov. 25, 2002.
Office Action dated Dec. 9, 2004, issued in co-pending U.S. Appl. No. 10/157,921, filed May 31, 2002.
Office Action dated Oct. 11, 2005, issued in co-pending U.S. Appl. No. 10/157,921, filed May 31, 2002.
Office Action dated Jul. 6, 2006, issued in co-pending U.S. Appl. No. 10/157,921, filed May 31, 2002.
Office Action dated Jun. 14, 2007, issued in co-pending U.S. Appl. No. 10/157,921, filed May 31, 2002.
Office Action dated May 12, 2002, issued in co-pending U.S. Appl. No. 10/157,921, filed May 31, 2002.
Alam H.B., Chen Z., Jaskille A., Querol R. I. L.C., Koustova E., Incencio R., Conran R., Seufert A., Ariaban N., Toruno K., and Rhee P. Application of a Zeolite Hemostatic Agent Achieves 100% Survival in a Lethal Model of Complex Groin Injury in Swine. J. Trauma. May 2004;56:974-983.
Holcomb J.B., McClain, Pusateri A.E., Beall D., Macaitis J.M., Harris R.A., MacPhee M.J., and Hess J.R. Fibrin Sealant Foam Sprayed Directly on Liver Injuries Decreases Blood Loss in Resuscitated Rats. J. Trauma Aug. 2000;49:246-250.
Ellis-Behnke R.G., Liang, Y.X., Tay D.K.C., Kau P.W.F., Schneider, G.E., Zhang S., Wu W., and So K.F. Nano hemoslat solution: immediate hemostasis at the nanoscale. Nanomedicine: Nanotechnology, Biology, and Medicine 2 (2006) 207-215.

* cited by examiner

METHOD AND KIT FOR INDUCING HYPOXIA IN TUMORS THROUGH THE USE OF A MAGNETIC FLUID

BACKGROUND OF THE INVENTION

The present invention is generally directed to treating tumors, and more particularly to a method of inducing hypoxia in tumors through the use of a magnetic fluid.

Tumors consist of a core of hypoxic (low oxygen) cells surrounded by a mass of non-hypoxic cells. The hypoxic cells form up to 30% of the tumor and are due to the poor, inadequate blood vessels that are formed to feed fast growing tumor cells. In order for a tumor to grow beyond a certain size, the tumor cells need oxygen and nutrients. Therefore, tumors are dependent on their vasculature to transport oxygen and nutrients in the blood to their cells. The growth of new blood vessels in tumors is termed angiogenesis.

Traditionally, cancerous tumors are treated by excision, chemotherapy, radiotherapy, or a combination of the three. However, each of these treatments has various disadvantages. Excision is impractical with a diffuse mass and impossible if tumors are located in a surgically inoperable area. Both chemotherapy and radiotherapy are nonspecific and inefficient as they target and kill both cancerous and benign cells. There are also various side effects associated with chemotherapy, such as hair loss and nausea. In addition, many cancerous cells develop drug resistance during chemotherapy and tumors often remain resilient throughout radiotherapy.

It has been proven that radiotherapy and chemotherapy are less effective in regions of hypoxic cells in tumors. In fact, hypoxic cells are three times more likely to resist radiation treatment. If non-hypoxic tumor cells are killed using radiotherapy or conventional chemotherapy, the tumor's previously dormant hypoxic cells may cause regeneration resulting in a more malignant, aggressive and treatment-resistant tumor. Administration of artificial oxidizing agents (nitroimidazoles) in combination with radiotherapy or chemotherapy, breathing of carbogen (an oxygen-rich gas) in combination with radiotherapy or chemotherapy, and hyperthermia are known methods of killing hypoxic tumor cells.

Angiogenesis suppressant drugs, such as endostatin and angiostatin, have been developed to slow or completely stop tumor growth. However, these drugs must be genetically engineered for clinical research, are difficult to maintain active in large quantities, and exhibit low stability under ambient conditions. Most importantly, anti-angiogenesis drugs alone may not kill all cells.

Another technique for killing tumor cells combines blocking the transport of oxygen and nutrients in blood to the cells with chemotherapy drugs. This technique is called transcatheter chemoembolization and is used to treat cancers of the liver. In transcatheter chemoembolization, a catheter is placed in the artery that supplies the tumor with blood and chemotherapy drugs and tiny sponge particles are injected into the catheter. The chemotherapy drugs kill the tumor cells while the sponge particles decrease the blood flow to the tumor and cause it to shrink. However, liver cells are somewhat hypoxic and while this treatment kills tumor cells of the liver, it may not be effective in tumors located in other areas of the body. The technique also does not kill all tumor cells and there is a high probability of reoccurance.

Other typical tumor treatments occlude blood flow to the tumor. There are four major types of devices designed to occlude blood flow to tumors: "glue," thrombosis producing particles, balloons, and coils. The term "glue" refers to compounds delivered to blood vessels which solidify on the walls of the blood vessels. These compounds typically solidify when they are exposed to electrolytes in the blood. Thrombosis producing particles are particles of polyvinyl alcohol, silicone polymer, proteins, glass, latex, silk suture material, or other materials which block blood vessels with diameters smaller than those of the particles. A balloon can be inserted into a blood vessel by a catheter or other means and then inflated to occlude blood flow in the vessel. Lastly, coils placed within a blood vessel present an obstacle to blood flow and induce blood clots thereon to stop blood flow.

However, all of these devices are subject to severe limitations. It is difficult to locate "glue" in a specific position as the cure rate of the "glue" varies. Thrombosis producing particles cannot block blood vessels with diameters larger than those of the particles, therefore, it is difficult to control the point of occlusion with thrombosis producing particles. Balloons may deflate or rupture the blood vessel and coils often fail to completely occlude blood flow. Complete occlusion might only be achieved with multiple coils and the use of multiple coils is costly and time consuming.

U.S. Pat. No. 5,646,185 discloses a method of treating a solid tumor including administering a compound which activates protein kinase C (PKC) to tumor such that the compound is directed to the hypoxic cells in the tumor. Compounds which activate PKC are selectively cytotoxic under hypoxic conditions. Suitable compounds which activate PKC include phorbol esters, diacylglycerols, and thapsigargin. The cells may be hypoxic either because of poor vascularization or the administration of a vasoconstrictive or vaso-occlusive agent. The vasoconstrictive agent may be a pharmaceutical vasoconstrictive compound such as an alpha adrenergic direct or indirect agonist. The vaso-occlusive agent may be a biodegradable or biocompatible vaso-occlusive agent, such as a cross-linked collagen, a cross-linked polyethylene glycol, a cross-lined polyactic acid, a cross-linked polyglycolic acid, or the like. Although compounds which activate PKC may be considered hypoxic drugs, this patent does not utilize magnetic fluids as the vasoconstrictive or vaso-occlusive agents.

Other forms of tumor treatment utilize magnetic fluids. Magnetic fluids are magnetic field responsive fluids containing magnetizable particles dispersed in a carrier liquid.

Two types of tumor treatments which utilize magnetic fluids are magnetic hyperthermia and magnetic drug delivery. U.S. Pat. Nos. 4,106,488; 4,303,636; 4,323,056; 4,545,368; 4,574,782; 4,662,359; 5,067,952; 5,108,359; 6,167,313 and 6,149,576 disclose magnetic hyperthermia, a process of passing an alternating magnetic field across a magnetic fluid in order to heat the particles within the magnetic fluid so that they destroy the tissue in their path. For example, U.S. Pat. No. 5,108,359 discloses a hemangioma treatment method comprising reducing the arterial blood flow to the hemangioma and administering a hard ferromagnetic substance to the hemangioma tissue wherein the hemangioma is under a magnetic field. Then the hemangioma is subject to an electromagnetic field of UHF frequencies or ultrasound energy as a hyperthermic treatment. In this patent, the hard ferromagnetic substance heats the tumor cells in the hyperthermic treatment. However, the success of magnetic hyperthermia has been hindered by the inability of current techniques to selectively heat many smaller visceral masses. It is also known in the art to chemically bind a drug to a ferrofluid, a type of magnetic fluid, and apply a magnetic field at the tumor site to direct and hold the drug at the tumor site (Lubbe, Cancer Res. 56: 4686 (1996)).

U.S. Pat. No. 5,236,410 discloses a tumor treatment method utilizing a ferrochemoembolizate. The arterial vessel that supplies the tumor is catheterized and a ferrochemoembolizate consisting of a magnetically hard ferromagnetic substance in a powder form, an oil medium, and an oil-soluble chemotherapeutic agent are injected into the catheter and consequently into the tumor. During injection, a local magnetic field is applied onto the tumor area. The injection lasts for about 1-5 minutes and the magnetic field is maintained for an extra 5-10 minutes. After 1-3 days, the tumor is also subjected to hyperthermia. Ultrahigh radio frequency electromagnetic field or ultrasonic waves are applied to the tumor to the temperature of 43.0°-43.5° C. for 5-45 minutes to ensure the death of the tumor cells. U.S. Pat. No. 5,236,410 also states that, in cases of large tumors it may be desirable to reduce blood flow with a metal coil in the tumor feeding blood vessel after administration of the chemoembolizate. However, in this patent the chemoembolizate alone does not ensure death of the tumor cells.

A method of treatment of hepatomas by the administration of a chemotherapeutic agent and ferromagnetic particles followed by hyperthermia is also known in the art (Sako M., Hirota S. Gan To Kagaku Ryoho, vol. 13, No. 4, pt. 2, 1618-1624 (1986)). A magnetic field acts to confines the chemotherapeutic agent and the ferromagnetic particles within the tumor.

In view of the drawbacks associated with present treatments, there is a need for a better technique for the treatment of tumor.

OBJECTS AND BRIEF SUMMARY OF THE INVENTION

The principal object of the present invention is to provide a method of treating tumors which overcomes the drawbacks associated with conventional treatments.

An object of the present invention is to provide a method of converting non-hypoxic cells to hypoxic cells by using a magnetic fluid.

Another object of the present invention is to provide a method of inducing hypoxia in a non-hypoxic region of a tumor by blocking a blood vessel feeding the tumor with a magnetic fluid and a device capable of generating a magnetic field.

An additional object of the present invention is to provide a method of treating tumors which in conjunction with a hypoxic drug ensures the death of the tumor cells and does not require the hyperthermia step.

Yet another object of the present invention is to provide a method of inducing hypoxia in a non-hypoxic region of a tumor by blocking a blood vessel feeding the tumor with a magnetic fluid and a device capable of generating a magnetic field in conjunction with a hypoxic drug in the tumor to kill tumor cells in all regions of the tumor. The hypoxic drug kills originally hypoxic, as well as originally non-hypoxic cells.

In summary, magnetic fluids are non-toxic and inexpensive and have demonstrated their usefulness in treating tumors. The present invention overcomes the shortcomings of the conventional treatments and kills tumor cells in all regions of the tumor. The present invention provides a method of inducing hypoxia in the non-hypoxic regions of tumors with magnetic fluids. Since this method ensures all regions of the tumor are hypoxic, it can be used in conjunction with hypoxic drugs to kill tumor cells in all regions of the tumor.

At least one of the above objects is met, in part, by the present invention, which in one aspect includes a method of converting non-hypoxic cells into hypoxic cells by impeding oxygen supply to non-hypoxic cells in a subject in need thereof by using a magnetic fluid.

Another aspect of the present invention includes a method of inducing a hypoxia in a non-hypoxic region of a tumor by administering a magnetic fluid in a subject in need thereof through a blood vessel feeding a tumor, and applying a magnetic field adjacent the tumor to join a plurality of particles in the magnetic fluid to form a blockage in the blood vessel thereby impeding the flow of blood to the tumor.

Another aspect of the present invention includes a method of treating a tumor by administering a magnetic fluid in a subject in need thereof through a blood vessel feeding a tumor, applying a magnetic field adjacent the tumor to join a plurality of particles in the magnetic fluid to form a blockage in the blood vessel thereby impeding the flow of blood to the tumor, and continuing to apply the magnetic field for a sufficient time to induce hypoxia in a non-hypoxic region of the tumor.

Another aspect of the present invention includes a kit for treating a tumor, including a quantity of core particles of a magnetic material and having an average diameter of about 1 nm to 20 µm, and a device for generating a magnetic field.

BRIEF DESCRIPTION OF THE DRAWINGS

The above and other objects, novel features and advantages of the present invention will become apparent from the following detailed description of the preferred embodiment(s) of the invention, as illustrated in the drawings, in which.

DETAILED DESCRIPTION OF THE PREFERRED EMBODIMENT(S) OF THE INVENTION

The present invention provides a method for inducing hypoxia in the non-hypoxic regions of a tumor by delivering a magnetic fluid to one or more blood vessels feeding the tumor and solidifying the magnetic fluid with a device capable of generating a magnetic field such that the magnetic fluid completely or partially blocks the flow of blood, oxygen, and nutrients to the tumor. Preferably, the properties of the magnetic fluid are tailored such that the magnetic fluid completely blocks the flow of blood, oxygen, and nutrients to the tumor.

Figure 1:
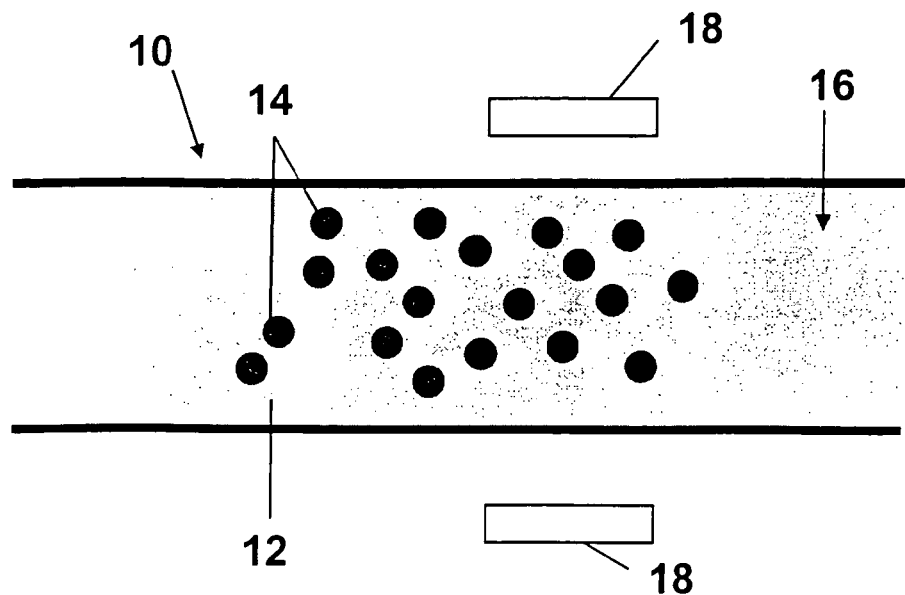
FIG. 1 is a schematic illustration of a portion of a blood vessel showing the conformation of the magnetic particles in the magnetic fluid not exposed to a magnetic field.

The magnetic fluid may be delivered to the tumor either through a catheter or by injection. A method, such as angiography in which a dye is injected into an area of the body to highlight blood vessels, may be used to identify and locate one or more blood vessels feeding the tumor. A catheter (not shown) is inserted into the blood vessel 10 that supplies a tumor and a magnetic fluid 12 is injected through the catheter (FIG. 1). If the magnetic fluid 12 is delivered to the tumor by injection, the magnetic fluid 12 may be injected into the blood vessel 10 that supplies the tumor or directly into smaller blood vessels supplying the tumor. As shown in FIG. 1, since a magnetic field does not yet act upon the magnetic fluid 12, the magnetic particles 14 within the magnetic fluid 12 remain freely suspended and do not block the flow of blood 16 through the blood vessel 10 to the tumor.

Figure 2:
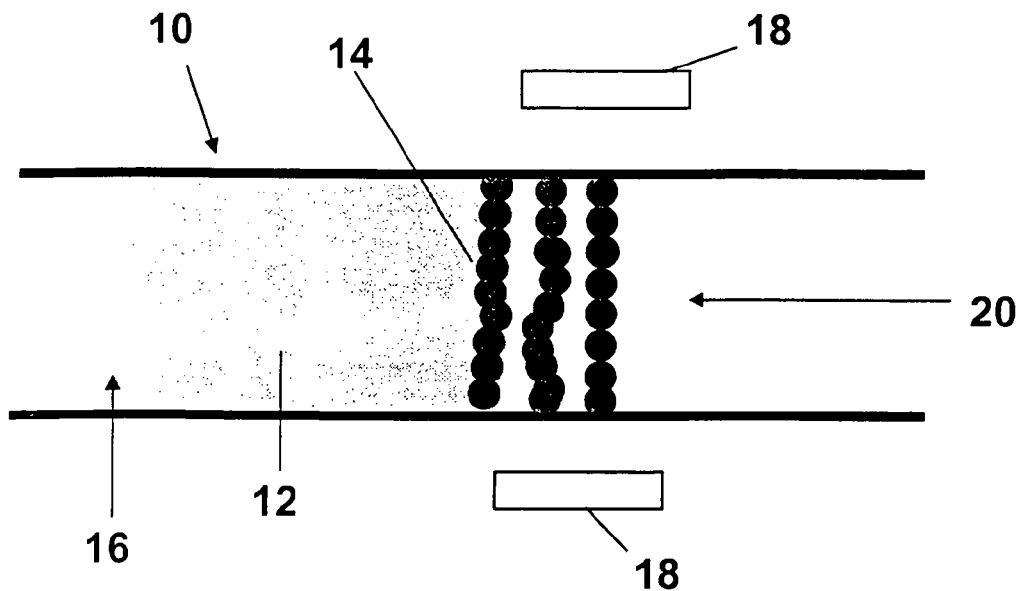
FIG. 2 is a view similar to FIG. 1, showing some of the particles magnetically coupled or joined to form blockages when exposed to a magnetic field.

Once inside the vasculature feeding the tumor, the magnetic fluid 12 is acted upon by a magnetic field generated by a device 18 capable of generating a magnetic field (FIG. 2).

The device 18 can be either internal or external to the body. For example, a micromagnet can be inserted at the tumor site or a magnet external to the body can be placed over the tumor site. Either a rare earth magnet or an electromagnet is an acceptable external magnet. As shown in FIG. 2, the magnetic field causes magnetic coupling of the particles 14 within the magnetic fluid 12 into chains or bent-wall like structures 20 that block the flow of blood 16 through the blood vessel 10 to the tumor. Consequently, the flow of oxygen and nutrients into the tumor is also blocked. After some time, the non-hypoxic regions/cells of the tumor become hypoxic (low in oxygen).

Preferably, one or more hypoxic drugs is used with this method of inducing hypoxia in the non-hypoxic regions of a tumor in order to kill tumor cells. (The term hypoxic drugs refers to pharmaceuticals that become active only under conditions of low oxygen.) The hypoxic drug may be delivered to the tumor either before or after the magnetic fluid 12 is delivered to the blood vessel(s) feeding the tumor. The hypoxic drug may also be delivered to the tumor with the magnetic fluid 12. For example, if a catheter is used to deliver the magnetic fluid 12, a combination of a hypoxic drug and the magnetic fluid 12 may be injected into the catheter. The hypoxic drug may be delivered either intravenously, through a catheter, or by injection. The hypoxic drug acts immediately in the hypoxic regions of the tumor and kills the hypoxic cells. Once the non-hypoxic regions of the tumor become hypoxic due to blocking of the blood vessel(s) by the magnetic fluid, the hypoxic drug becomes active and kill these tumor cells. Therefore, the hypoxic drug kills all tumor cells, those in originally hypoxic regions, as well as those in originally non-hypoxic regions. The hypoxic drugs that may be used in the present invention include, but are not limited to, AQ4N (1,4-bis-{[2-(dimethylamino-N-oxide)ethyl]amino}5,8-dihydroxyanthracene-9,10-dione), bioreductive alkylating agents such as mitomycin C, porfiromycin, and tirapazamine.

The magnetic particles for use in the present invention may be synthesized by various methods, such as chemical synthesis, sol-gel, chemical co-precipitation and microwave plasma technique. The microwave plasma technique, described in U.S. Pat. No. 6,409,851 by Sethuram et al. (incorporated herein in its entirety by reference) is the preferred technique as it is unique in that it gives better control over particle size, shape and purity, and can be readily extended to produce different compositions of powders. The composition includes a carrier medium and a particulate material of coated core particles, such as iron, iron oxide, cobalt, cobalt oxide, nickel, nickel oxide, or an alloy or a combination thereof. Preferably, the particulate material includes core particle of iron and its oxides.

The average diameter or size of the particles can be from about 1 nm to 20 μm. The preferred size is about 10 nm to 5 μm, while the most preferred size is about 10 nm to 1000 nm. The size of the particles is directly related to toxicity, as the particles should be large enough so that they do not get absorbed inside the body, and yet small enough to escape the immunological response of the macrophages. In addition, the particle size also directly translates into the magnetic mass of the mixture, thereby affecting the magnetic properties.

Figure 3:
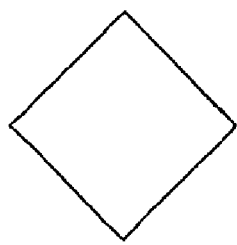
FIG. 3 illustrates various shapes of the magnetic particles for use in the present invention.
Figure 3:
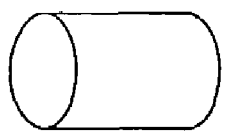
Figure 3:
Figure 3:
Figure 3:
Figure 3:
Figure 3:
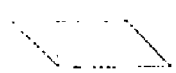
Figure 3:
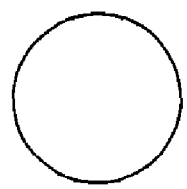

The shape of the particles is important for two reasons. First, the magnetic effect is dependent upon the particle volume fraction, which in turn is a function of the particle shape. For instance, needle-shaped particles exhibit similar magnetic effect at concentrations ten times smaller than spherical particles because of larger surface area per volume. Second, the flow characteristics of the particles in a liquid medium are dependent upon their shape. The shapes utilized in this invention include, but are not limited to, spherical, needle-like, cubic, irregular, cylindrical, diamond, oval, or a combination thereof. FIG. 3 shows preferred particle shapes.

In the present invention, one or more surface coatings on the particles serve several purposes, such as preventing particle agglomeration, rendering the particles biocompatible, and preventing dissolution of the magnetic materials. The types of coatings that may be utilized in the present invention, include silica, gold, a polymer, or a combination thereof. The polymer can be polyethylene glycol, dextran, Tween®, sorbitol, mannitol, or a combination thereof. The coatings are preferred as they can be functionalized and are non-toxic. The most preferred coating is silica or gold, as they are both effectively inert with respect to dissolution in biological fluids.

Colloidal particles have an inherent tendency to aggregate and form clusters or agglomerate due to attractive van der Waals (vdW) forces. To stabilize the particles against these attractive forces, it is necessary to introduce a repulsive interparticle force, either by an electrostatic or a steric means. Electrostatic stabilization utilizes the surface charge typically present on the particles, which is effective in a medium having a high dielectric constant, such as water, while in steric stabilization, a sufficiently thick layer of a polymeric or surfactant molecules is introduced around the particles. The surface layer functions as a steric barrier to particle aggregation, and thereby ensures the stability of the fluid. This technique is preferred for the present invention. The steric stabilizer for the particles are chosen from, but are not limited to, polyethylene oxide (PEO), dextran, and Pluronic® surfactants (available from BASF). The magnetic particles are preferably coated with a surfactant by physical or chemical adsorption in a solution phase.

The coated particles are dispersed in a carrier liquid by high-speed shear mixing and ultrasonification to form a homogeneous fluid. Suitable carrier liquid includes water, Ringer's solution, normal saline, sugar solution, blood plasma, or a combination thereof.

Preferably, the particulate weight or volume fraction in the magnetic fluid is from about 1% to 90%. The particulate volume or weight fraction partially determines the magnetic properties of the magnetic fluid. A magnetic fluid with a greater particulate weight or volume fraction exhibits more magnetic susceptibility, but a greater zero field viscosity. The term zero field viscosity refers to the viscosity of the magnetic fluid when it is not exposed to a magnetic field. In the present invention, the zero field viscosity cannot be so large that the magnetic fluid loses fluidity as the magnetic fluid must travel to blood vessels feeding the tumor. Other factors which influence the magnetic properties of the magnetic fluid include particle composition and shape. The particulate weight or volume fraction and the composition and shape of the particles may be tailored to obtain desired rheological and magnetic properties of the magnetic fluid such that the magnetic fluid completely blocks blood flow to the tumor.

EXAMPLE

Ultrafine powders of iron with a particle size less than about 20 nm were produced using the proprietary microwave plasma chemical synthesis process described in U.S. Pat. No. 6,409,851 by Sethuram et al. Vapors of iron pentacarbonyl were fed into the plasmatron with argon as the plasma gas. The plasma gas flow rate was about 0.003-0.0034 $m^3$/min and that of the carrier gas was about 0.0003-0.0004 $m^3$/min. The plasma temperature was about 900-950° C., the powder feed rate was about 50-60 gm/hr, and the quenching water flow rate was about 2.0-2.5 liter/min at about 20° C. The reactor column diameter was about 48 mm and its length was about 10". The microwave forward power was about 4 kW, the reflected power was about 0.7 kW, and the operating frequency was about 2450 MHZ.

The iron particles were coated with dextran in solution phase and dispersed in water by high-speed shear mixing and ultrasonification.

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. A method of inducing hypoxia in a non-hypoxic region of a tumor, comprising the steps of:
   a) administering a magnetic fluid in a subject in need thereof through a blood vessel feeding a tumor; and
   b) applying a magnetic field adjacent the tumor to join a plurality of particles in the magnetic fluid to form a blockage in the blood vessel thereby impeding the flow of blood to the tumor.

2. The method of claim 1, wherein:
the magnetic fluid in step a) is delivered through a catheter or by injection.

3. The method of claim 1, wherein:
the magnetic field in step b) is applied by an internal micromagnet, an external rare earth magnet, or an external electromagnet.

4. The method of claim 1, wherein:
the magnetic fluid comprises core particles of a magnetic material.

5. The method of claim 4, wherein:
the core particles comprise coated particles.

6. The method of claim 4, wherein:
the core particles have an average diameter of about 1 nm to 20 µm.

7. The method of claim 6, wherein:
the core particles have an average diameter of about 10 nm to 5 µm.

8. The method of claim 7, wherein:
the core particles have an average diameter of about 10 nm to 1,000 nm.

9. The method of claim 6, wherein:
the core particles are dispersed in a carrier fluid.

10. The method of claim 9, wherein:
the carrier fluid comprises a water-based carrier fluid.

11. The method of claim 9, wherein:
the carrier fluid is selected from the group consisting of water, Ringer's solution, normal saline, sugar solution, blood plasma, and a combination thereof.

12. The method of claim 9, wherein:
the fraction of the core particles is about 1-90%.

13. The method of claim 6, wherein:
the core particles comprise a general shape selected from the group consisting of spherical, needle-like, cubic, irregular, cylindrical, diamond, oval, and a combination thereof.

14. The method of claim 4, wherein:
the magnetic material is selected from the group consisting of iron, iron oxide, cobalt, cobalt oxide, nickel, nickel oxide, an alloy, and a combination thereof.

15. The method of claim 4, wherein:
the core particles comprise a coating of a surfactant.

16. The method of claim 15, wherein:
the surfactant is selected from the group consisting of polyethylene oxide, dextran, polyoxypropylene-polyoxyethylene block copolymer, and a combination thereof.

17. The method of claim 4, wherein:
the core particles comprise a coating selected from the group consisting of a ceramic material, a metallic material, a polymer material, and a combination thereof.

18. The method of claim 17, wherein:
the coating is selected from the group consisting of silica, gold, silver, platinum, steel, cobalt, carbon, polyethylene glycol, dextran, polyoxyethylene sorbitol ester, sorbitol, mannitol, and a combination thereof.

19. The method of claim 4, wherein:
the core particles comprise first and second successive coatings.

20. The method of claim 19, wherein:
the first coating comprises a coating of a surfactant; and
the second coating comprises a coating of a material selected from the group consisting of a ceramic material, a metallic material, a polymer material, and a combination thereof.

21. The method of claim 20, wherein:
the surfactant is selected from the group consisting of polyethylene oxide, dextran, polyoxypropylene-polyoxyethylene block copolymer, and a combination thereof.

22. The method of claim 21, wherein:
the second coating is selected from the group consisting of silica, gold, silver, platinum, steel, cobalt, carbon, polyethylene glycol, dextran, polyoxyethylene sorbitol ester, sorbitol, mannitol, and a combination thereof.

23. A method of treating a tumor, comprising the steps of:
a) administering a magnetic fluid in a subject in need thereof through a blood vessel feeding a tumor;
b) applying a magnetic field adjacent the tumor to join a plurality of particles in the magnetic fluid to form a blockage in the blood vessel thereby impeding the flow of blood to the tumor; and
c) continuing with step b) for a sufficient time to induce hypoxia in a non-hypoxic region of the tumor.

24. The method of claim 23, further comprising the step of:
d) administering a hypoxic drug prior to or after step a), or substantially simultaneously therewith.

25. The method of claim 24, wherein:
the hypoxic drug is selected from the group consisting of AQ4N, mitomycin C, porfiromycin, and tirapazamine.

26. The method of claim 24, wherein:
the hypoxic drug is administered through a catheter, by injection, or intravenously.

27. The method of claim 23, wherein:
the magnetic fluid is delivered through a catheter or by injection.

28. The method of claim 23, wherein:
the magnetic field is applied by an internal micromagnet, an external rare earth magnet, or an external electromagnet.

29. The method of claim 23, wherein:
the magnetic fluid comprises core particles of a magnetic material.

30. The method of claim 29, wherein:
the core particles comprise coated particles.

31. The method of claim 29, wherein:
the core particles have an average diameter of about 1 nm to 20 μm.

32. The method of claim 31, wherein:
the core particles have an average diameter of about 10 nm to 5 μm.

33. The method of claim 32, wherein:
the core particles have an average diameter of about 10 nm to 1,000 nm.

34. The method of claim 31, wherein:
the core particles are dispersed in a carrier fluid.

35. The method of claim 34, wherein:
the carrier fluid comprises a water-based carrier fluid.

36. The method of claim 34, wherein:
the carrier fluid is selected from the group consisting of water, Ringer's solution, normal saline, sugar solution, blood plasma, and a combination thereof.

37. The method of claim 34, wherein:
the fraction of the core particles is about 1-90%.

38. The method of claim 31, wherein:
the core particles comprise a general shape selected from the group consisting of spherical, needle-like, cubic, irregular, cylindrical, diamond, oval, and a combination thereof.

39. The method of claim 29, wherein:
the magnetic material is selected from the group consisting of iron, iron oxide, cobalt, cobalt oxide, nickel, nickel oxide, an alloy, and a combination thereof.

40. The method of claim 29, wherein:
the core particles comprise a coating of a surfactant.

41. The method of claim 40, wherein:
the surfactant is selected from the group consisting of polyethylene oxide, dextran, polyoxyethylene sorbitol ester, and a combination thereof.

42. The method of claim 29, wherein:
the core particles comprise a coating selected from the group consisting of a ceramic material, a metallic material, a polymer material, and a combination thereof.

43. The method of claim 42, wherein:
the coating is selected from the group consisting of silica, gold, silver, platinum, steel, cobalt, carbon, polyethylene glycol, dextran, polyoxyethylene sorbitol ester, sorbitol, mannitol, and a combination thereof.

44. The method of claim 29, wherein:
the core particles comprise first and second successive coatings.

45. The method of claim 44, wherein:
the first coating comprises a coating of a surfactant; and
the second coating comprises a coating of a material selected from the group consisting of a ceramic material, a metallic material, a polymer material, and a combination thereof.

46. The method of claim 45, wherein:
the surfactant is selected from the group consisting of polyethylene oxide, dextran, polyoxypropylene-polyoxyethylene block copolymer, and a combination thereof.

47. The method of claim 46, wherein:
the second coating is selected from the group consisting of silica, gold, silver, platinum, steel, cobalt, carbon, polyethylene glycol, dextran, polyoxyethylene sorbitol ester, sorbitol, mannitol, and a combination thereof.

* * * * *